United States Patent [19]

Childers et al.

[11] Patent Number: 4,909,988

[45] Date of Patent: Mar. 20, 1990

[54] STEAM EFFICIENT PREVACUUM STERILIZER CYCLE

[75] Inventors: Robert W. Childers, Erie; Thomas G. Cook, Fairview; David A. Karle, McKean; Ronald P. Krahe, Girard; George E. Sparber, Linesville; Gerald L. Yeaney, Erie, all of Pa.

[73] Assignee: American Sterilizer Company, Erie, Pa.

[21] Appl. No.: 113,090

[22] Filed: Oct. 23, 1987

Related U.S. Application Data

[62] Division of Ser. No. 759,539, Jul. 26, 1985, Pat. No. 4,808,377.

[51] Int. Cl.$^4$ ............................................. A61L 2/06
[52] U.S. Cl. ...................................... 422/26; 422/116
[58] Field of Search ................................. 422/26, 116

[56] References Cited

U.S. PATENT DOCUMENTS

| | | | |
|---|---|---|---|
| 3,494,725 | 2/1970 | Irons et al. | 422/26 |
| 4,296,067 | 10/1981 | Näsman et al. | 422/26 |
| 4,372,916 | 2/1983 | Chamberlain et al. | 422/116 X |
| 4,687,635 | 8/1987 | Kaehler et al. | 422/26 |
| 4,759,909 | 7/1988 | Joslyn | 422/116 X |
| 4,770,851 | 9/1988 | Joslyn | 422/26 |

Primary Examiner—Barry S. Richman
Assistant Examiner—Jill Johnston
Attorney, Agent, or Firm—Kirkpatrick & Lockhart

[57] ABSTRACT

A self-contained, closed loop steam sterilizer has an integral external boiler. The sterilizer employs a prevacuum sterilization cycle with a dwell phase to promote steam efficiency. A single pump accomplishes all pumping functions in a prioritized manner.

2 Claims, 5 Drawing Sheets

STEAM EFFICIENT PREVACUUM STERILIZER CYCLE

This is a divisional of co-pending application Ser. No. 759,539 filed on July 26, 1985, now U.S. Pat. No. 4,808,377.

BACKGROUND OF THE INVENTION

1. Field of the Invention

This invention relates to a self-contained, closed loop steam sterilizer having an integral external boiler and requiring only a single electrical connection for its operation.

2. Description of the Prior Art

With the proliferation of ambulatory patient care centers which perform many medical procedures heretofore associated only with hospitals, there is a need to sterilize goods in such centers that traditionally have been sterilizable only in large hospital sterilizers with unlimited steam supplies. These goods primarily are surgical packs and wrapped goods which require reliable steam penetration of the goods to acheive sterility. The existing sterilizers that generate steam within the sterilization chamber itself are not recommended for these types of loads.

Ambulatory care centers tend to be small compared with conventional hospitals and thus sterilizer cost and size, as well as steam conservation, are important considerations in the ability of an ambulatory care center to function. There exists, therefore, a need for a compact, inexpensive steam sterilizer capable of sterilizing surgical packs while, at the same time, not being dependent on an elaborate and expensive external steam source. This need was partially met by the sterilizer described in Proceedings, Association for the Advancement of Medical Instrumentation, 17th Annual Meeting, San Francisco, May 9–12, 1982. "Sterilization Equipment in Support of the Army in the Field", Young, J. The need is more fully met by the self-contained, closed loop steam sterilizer disclosed herein.

SUMMARY OF THE INVENTION

The present invention relates to a self-contained, steam sterilizer having an integral, external steam generating means. The sterilizer includes components for carrying out a prevacuum sterilization cycle with a dwell phase. The pumping functions in the sterilizer are served by a single pump; those functions are prioritized and synchronized to provide a dynamic boiler fill system. Condensate formed in the sterilizer is conserved in closed loops. A unique water reservoir may be filled by the use of system components. Venturis in sterilizer piping provide novel advantages.

DETAILED DESCRIPTION OF THE PREFERRED EMBODIMENTS

General Description

Figure 1:
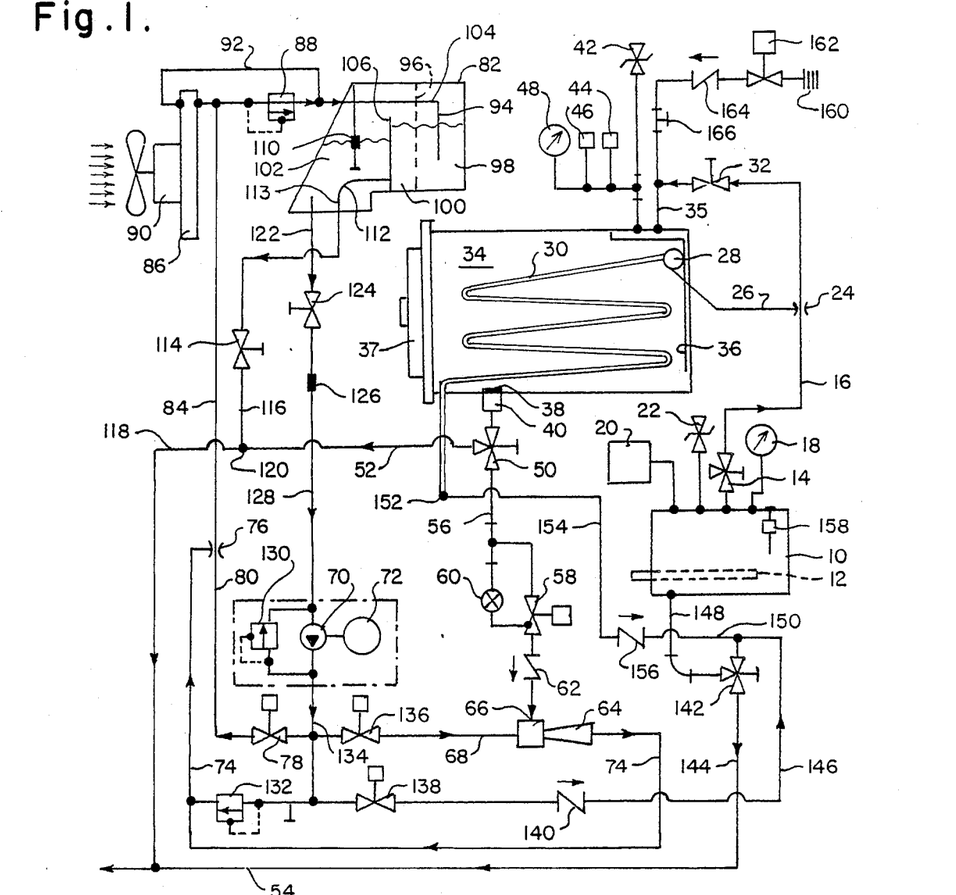
FIG. 1 is a schematic of the self-contained, closed loop steam sterilizer disclosed herein.

Referring to FIG. 1, there is shown a schematic diagram of the components of the steam sterilizer of the present invention. As shown in FIG. 1, the sterilizer employs a closed loop steam generating system which includes boiler 10 as the steam generating means. A resistance heating element 12 energized by a source of electric power heats the water present within boiler 10 and converts into steam; as steam is generated within boiler 10, the pressure of the steam increases. The path for steam flow out of boiler 10 is through shut-off valve 14 and into line 16. A steam pressure guage 18 is provided on boiler 10 for monitoring steam pressure within boiler 10. When the steam pressure reaches a predetermined level, pressure control switch 20 is actuated to cut off the flow of electrical current to heating element 12. As the temperature within boiler 10 decreases due to the effects of convection and radiation, the steam pressure decreases; when a predetermined lower pressure is reached, pressure controller 20 energizes heating element 12 to again generate steam within boiler 10. A poppet-type, spring loaded steam safety valve 22 is provided on boiler 10 to accomodate any overpressure situation should pressure controller 20 fail to operate.

A venturi tube 24 is provided in line 16; the venturi is actually a "T" connection which permits steam to flow upwardly (in the direction of the arrow) to steam solenoid valve 32 and also through line 26 in a direction toward manifold 28 and chamber 34. Chamber 34 having a door 37 is equipped with tracer coils 30 (actually four in number although only two coils 30 are shown in FIG. 1). Tracer coils 30 heat the walls of chamber 34 to offset heat losses brought about by radiation. Steam flows into coils 30 from line 26 through a manifold 28.

When it is desired to introduce steam into chamber 34, steam solenoid valve 32 is opened and steam flows through line 35; a baffle 36 is provided within chamber 34 to prevent the steam from impinging directly on the load of goods to be sterilized. As steam is introduced into chamber 34, it pushes air within chamber 34 down and out through strainer 38 and past thermister 40 which measures the temperature of any fluid in contact with it.

Chamber 34 is provided with a steam pressure safety valve 42; this valve is present to vent steam during a severe overpressure situation. The steam pressure within chamber 34 is not controlled directly as a function of pressure but by the temperature. Switch 44 is a 1 psi switch; this switch is used to signify a sufficiently low pressure within chamber 34 that it is safe to open door 37. Switch 46 is a vacuum switch which actuates selected control circuitry when the vacuum within chamber 34 reaches a predetermined level. A pressure guage 48 permits monitoring the pressure within chamber 34.

Fluids leaving chamber 34 through strainer 38 encounter a 3-way draincock 50. One path of flow through draincock 50 is through line 52 to a cleaning drain hose 54 which can be connected to a remote drain. This branch would be used in cleaning chamber 34. The other path of flow through draincock 50 is via line 56 which forms part of a closed loop system.

A parallel flow path is provided in line 56; one path is through drain solenoid valve 58 and the other path is through steam trap 60. When drain solenoid valve 58 is closed, the effect is to trap steam in chamber 34 and permit it to flow out only through steam trap 60. Steam trap 60 operates thermostatically, independent of drain solenoid 58, to open when condensate or air, both at lower temperature than steam, is present. After permitting passage of the air and/or condensate, steam trap 60 returns to its normally closed position. When drain solenoid valve 58 is open, a direct path is provided for fluids to leave chamber 34; these fluids pass through check valve 62 and to the suction port 66 of water ejector 64. Any time steam is flowing through check valve 62, water is flowing through ejector 64 so that the steam is immediately condensed in ejector 64. This immediate condensation of steam tends to permit the sterilizer to operate more quietly.

The flow of water through ejector 64, from inlet 68 to outlet line 74, is caused by water pump 70 which is driven by electric motor 72. Water leaving ejector 64 typically contains very little steam. Water flowing through line 74 passes through the suction port of a venturi "Y" 76. The flow of water through the straight portion of venturi "Y" 76 is brought about by the opening of heat exchanger solenoid valve 78 and the pumping of water therethrough by pump 70 into line 80. When water flows through line 80 a slight back pressure or suction is created at venturi "Y" 76 which prevents the reverse flow of water in line 74, i.e. through ejector 64 and back into chamber 34. Water flowing through line 74 combines with any water flow in line 80.

Water flowing through either line 74 or line 80 flows upwardly through line 84 toward water tank 82. Normally water flows from line 84 into heat exchange core 86 where the water is cooled by the flow of air caused by fan 90. A relief valve 88 in parallel with heat exchange unit 86 opens upon the occurrence of any pressure spike to protect core 86.

Water leaving heat exchange core 86 passes through line 92 and enters water tank 82 through line 94. Line 94 discharges the water in the receiving section 98 of water tank 82 below the surface of the water in that section so that any residual steam will be condensed. The receiving section 98 of water tank 82 is separated from the settling section 100 by a screen 96. Line 94 includes at least one vacuum break hole 104 which prevents the backflow of water from water tank 82 to chamber 34 when pump 70 is off. The third section of water tank 82 is a suction section 102.

Air is discharged from water tank 82 through vent 108. Air release is enhanced by providing for thin section flow of water from settling tank 100 over weir 106 and into suction section 102. Dual float switch 110 is mounted in suction section 102; float switch 110 detects when water tank 82 is full and empty. A tube 112 extends through suction section 102 and into settling portion 100. This tube has holes 113 drilled in its vertical portion. The purpose of tube 112 is to permit draining of all sections of water tank 82 through shutoff valve 114, into lines 116 and 118, and then to cleaning drain hose 54.

Water for supplying pump 70 is withdrawn from water tank 82 through line 122, the inlet of which is above the floor of suction section 102. A shut-off valve 124 is provided in line 122. A temperature sensor 126 also is provided in line 122. Water is drawn from suction section 102 by pump 70 to the inlet 128 of pump 70. An integral relief valve 130 is provided in pump 70 to protect the pump seals in case of malfunction. A second external relief valve 132 is provided in parallel with pump 70 to protect it from overheating in case of malfunction.

Water leaves pump 70 through outlet 134 and can supply any one of three items: (a) ejector solenoid valve 136; (b) heat exchanger solenoid valve 78; (c) boiler feed solenoid valve 138. Water flowing to boiler 10, after passing boiler feed solenoid 138, passes check valve 140, through line 146 to 3-way valve 142, and through line 148 to boiler 10.

Coils 30 join one another below chamber 34 at collection point 152. Condensate collected from coils 30 then flows through line 154 to check valve 156, through line 150 to valve 142, and into boiler 10 through line 148.

Dual float switch 158 is provided in boiler 10 to sense when boiler is full (thereby protecting it against overfilling), when the boiler is not full (thereby causing it to refill), and when boiler is at low water level (thereby protecting heating element 12 from overheating because it is out of cooling contact with water).

Air may be admitted to chamber 34 through air filter 160, through air solenoid 162 and check valve 164, past service tap 66 and into chamber 34 through line 35. At the end of a sterilization cycle, air is admitted to chamber 34 to bring it to atmospheric so that the door 37 can be opened.

Sterilizer Start-Up

When a steam sterilizer has not been run for a period of time, it is desirable to bring the walls of the sterilizer chamber to an elevated temperature before commencing the operation of the first sterilizing cycle. If this procedure is not followed, the steam entering the sterilizer chamber condenses upon contact with the cool chamber roof, the condensate drops onto the load, and a condition known as "wet packs" occurs.

Heat may be supplied to the walls of the sterilizing chamber by the traditional means of providing a jacket around the chamber walls and passing steam through the jacket. Alternatively, heating may be supplied by tracing coils surrounding the exterior of the chamber. The latter means of heating the chamber walls is depicted in the drawings wherein the tracing coils are designated by the reference numeral 30.

Figure 2:
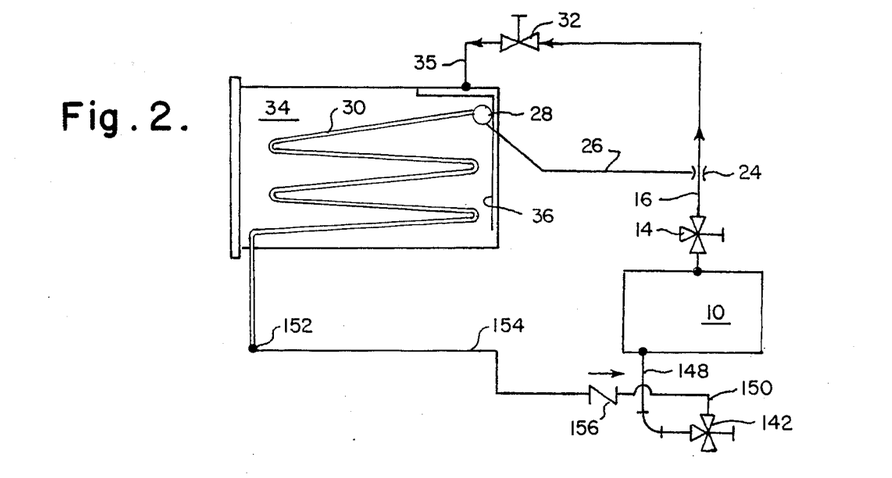
FIG. 2 is a schematic of components shown in FIG. 1 that are used to purge air from the sterilizer chamber wall heating means during start-up.

Whether the heating means be a jacket or tracing coils, it is important to first purge air from the interior thereof; otherwise, they will not heat up upon the introduction of steam. One technique for accomplishing an air purge is to force the air through a thermostatic steam trap. By reference to FIG. 2, a method to purge tracing lines of air where no trap is present will be described;

the method disclosed would work equally well with a jacketed sterilization chamber.

Upon energizing boiler 10, which may be integral as shown in the drawings or external, steam is generated and is permitted to pass through valve 14 and line 16 to venturi "T" 24 where steam flow branches into two flow paths: a first path through line 26, manifold 28 and into tracing coils 30 where it compresses any air present in the coils; and a second path directly through venturi 24 to steam solenoid valve 32 where the flow is stopped because valve 32 is closed. The boiler 10 continues to generate steam until full steam pressure (about 70 psi) is reached. The sterilizer control system (not shown in FIGS. 1 or 2) signals the opening of steam solenoid valve 32 to admit steam into chamber 34 via line 35 and around and through baffle 36. After a predetermined period, say one minute, steam solenoid valve 32 is closed and the boiler is permitted to recover (attain its steam full pressure) and then steam solenoid valve 32 is opened again for the same predetermined period. Each time valve 32 is opened, the flow of steam through venturi 24 creates a suction in line 26 which draws steam and air out of coils 30 to be joined with the main steam flow into chamber 34. After successive pulses of this type, perhaps 7 or 8, substantially all of the air has been removed from coils 30. The air thus removed flows into the chamber 34 and out of the chamber drain.

Figure 3:
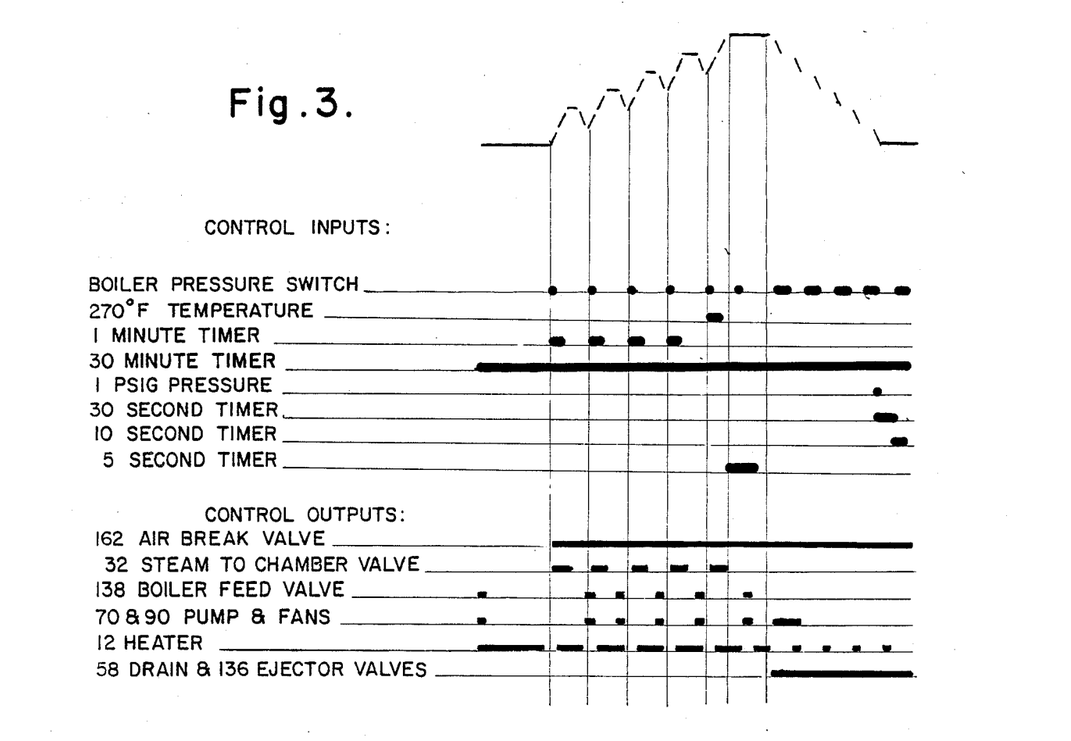
FIG. 3 is a chart illustrating the operating sequence of the components shown in FIG. 2.

The foregoing sequence is depicted in conventional chart form in FIG. 3.

Method for Prioritizing the Pumping Functions in a Self-Contained, Closed-Loop Steam Sterilizer In known self-contained steam sterilizers having integral boilers, the requirement for pumping fluids has been met by providing separate pumps, each sized according to the particular pressure and flow requirements of their respective functions. This design strategy obviously adversely impacts the ultimate cost, weight and overall size of the sterilizer.

Figure 4:
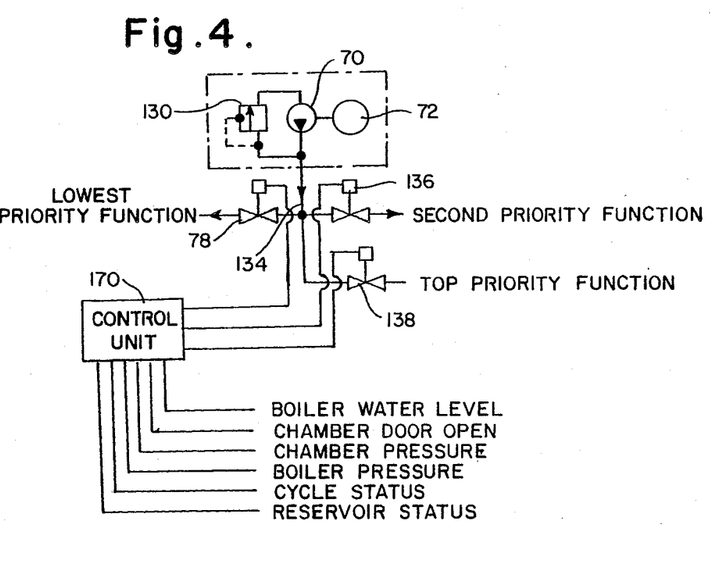
FIG. 4 is a schematic illustrating a system for prioritizing the pumping functions of the sterilizer shown in FIG. 1.

As shown in FIG. 4, the present sterilizer incorporates, as do many, a microprocessor 170 to control the sterilization cycle which will be described in detail hereinafter. The availability of microprocessor 170 makes possible a radical departure from the aforementioned design strategy by permitting the use of a single pump capable of serving any pumping function selected.

As shown in FIG. 4, the output of the single pump 70 is connected in parallel to (i) the boiler feed circuit through boiler feed solenoid valve 138; (ii) the chamber evacuation circuit through ejector solenoid valve 136; and (iii) the recirculating/cooling circuit through heat exchange solenoid valve 78. By appropriate programming of microprocessor 170, any of the foregoing circuits may be energized or disabled by opening or closing the corresponding solenoid valve. Such a time-shared pumping system results in substantial conservation of cost, weight and size.

As indicated on FIG. 4, the three pumping functions are prioritized in the order that is listed above; namely, boiler feed is given top priority because the boiler 10 in the present sterilizer must be refilled at various times during a single sterilization cycle; that is, boiler 10 is sized in favor of being less expensive, more compact and lighter than a boiler capable of generating sufficient steam to serve a complete sterlization cycle without refilling. Boiler 10 thus suffers less energy loss due to conduction, convection and radiation effects. The next priority is the evacuation circuit and last priority is the recirculation/cooling circuit.

Conventional microprocessor 170, as shown in FIG. 4, is fed by various input sensors such as boiler water level, chamber door open, etc. in a well-known manner. Based on the condition of these various inputs, the prioritizing function is exercised. Further, the three pump functions may be synchronized during a sterilization cycle in a manner to be described hereinbelow.

Prevacuum Sterilization Cycle

Figure 5:
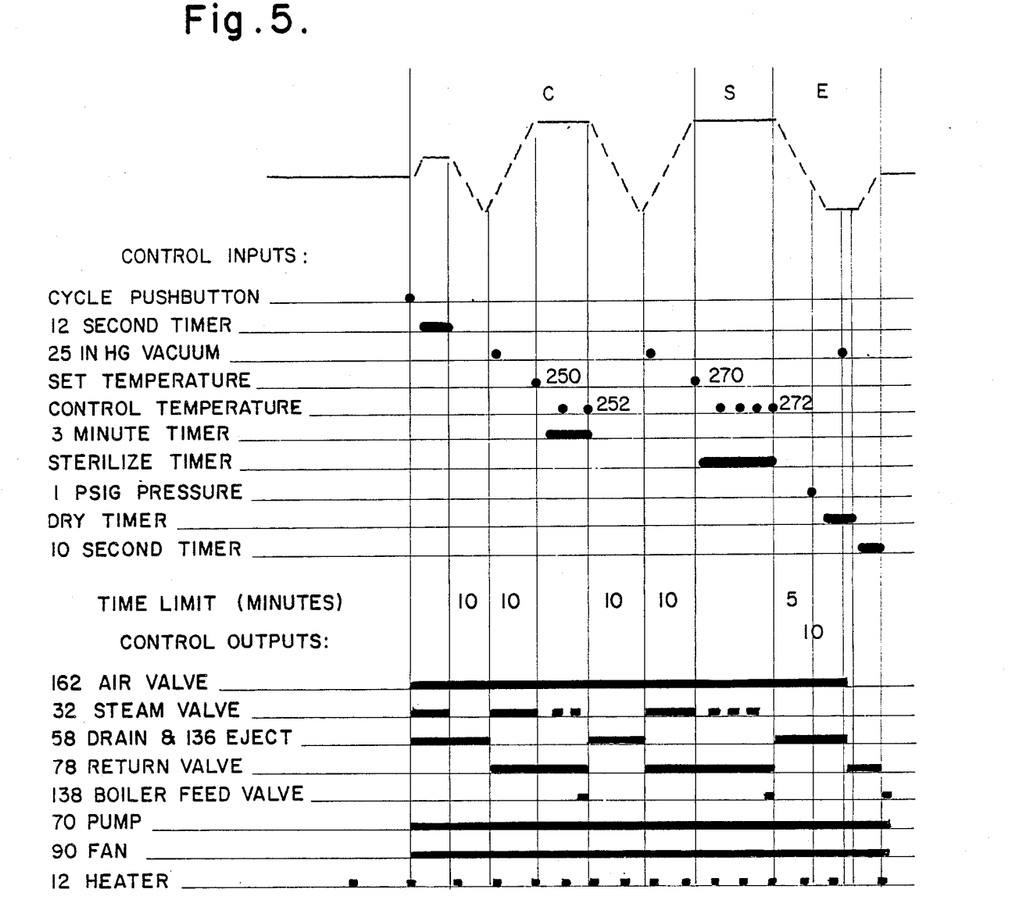
FIG. 5 is a chart illustrating the sterilization cycle employed in the sterilizer of FIG. 1.

Referring to FIG. 5, there is shown in conventional form the sterilization cycle used with the self-contained, closed-loop sterilizer described herein. The cycle differs from known sterilization cycles employing a prevacuum step in that the known cycles make no serious attempt to conserve steam; as a result, prevacuum sterilization cycles are difficult to run with small electric steam generators.

The cycle is initiated by actuating the cycle pushbutton. A 12 second timer is started and the drain is opened; i.e. drain solenoid valve 58 is opened, pump 70 is actuated and ejector solenoid valve 138 is opened. At the same time, steam is introduced into chamber 34 by the opening of steam solenoid valve 32. During the 12 second period, air is being positively displaced from chamber 34 by entering steam. At the end of 12 seconds, the cycle immediately proceeds to an evacuation step by closing steam solenoid valve 32 and permitting ejector 64 to withdraw steam and the remaining air from chamber 34. The evacuation proceeds until the 25 in. hg vacuum switch 46 is tripped. If switch 46 is not tripped within a 10 minute period, the operator is signalled to suggest that some malfunction has occurred.

After switch 46 is tripped, the cycle enters a charge phase by opening steam solenoid valve 32 to admit steam to chamber 34; at the same time, drain solenoid valve 58 is closed and ejector 64 is de-energized. The charge phase continues until the chamber temperature reaches 250° F. The cycle then proceeds to a 3 minute dwell phase during which the chamber temperature is maintained between 250° F. and 252° F.

The dwell period materially aids in conditioning the load thus making unnecessary the drawing of deep vacuums or additional shallower vacuums as is the case in known prevacuum cycles. At the end of 3 minutes, the cycle proceeds to an exhaust and evacuation phase; at this time, steam solenoid valve 32 is closed, drain solenoid valve 58 is opened and ejector 64 is energized. Again there is a 10 minute time limit to reach 25 in. hg of vacuum. When switch 46 is tripped, the cycle enters another charge phase; steam solenoid valve 32 is opened while drain solenoid valve 58 is closed and ejector 64 is de-energized. When a temperature in chamber 34 of 270° F. is reached, the cycle proceeds into the sterilization phase with the temperature being maintained between 270° F. and 272° F. The interval of the sterilization phase is 4 minutes; if within that period, the temperature drops to 270° F. as reflected by a pressure decrease within chamber 34, steam solenoid valve 32 is opened to admit more steam to chamber 34 and remains open until a temperature at 272° F. is recorded.

At the end of the sterilization phase, the cycle proceeds into an exhaust and evacuation phase; steam solenoid valve 32 is closed, drain solenoid valve 58 is opened and ejector 64 is energized. When the pressure within chamber 34 reaches 1 psi, switch 44 is tripped and a dry timer, set for a predetermined interval, is started. The evacuation proceeds until switch 46 is tripped, indicating the attainment of 25 in. hg. At the end of the drying period, air solenoid valve 162, which is normally closed, is opened to admit air to chamber 34. 10 seconds after air solenoid valve 162 is opened, the cycle complete light comes on, signaling the operator that it is safe to open chamber door 37.

It may be noted from FIG. 5, that pump 70 and fan 90 are in constant operation throughout the cycle. Heater 12 comes on and goes off as needed to maintain at least 70 psi of steam pressure in boiler 10.

A separate feature of the cycle is the dynamic boiler fill. During the cycle, there will be times when the boiler water level is not full as indicated by dual float switch 158. When this situation exists, the boil feed solenoid valve 148 will be opened as soon as boiler heater 12 goes off. In practice, the boiler feed sequence will occur during (i) an evacuation phase by the boiler feed function momentarily taking priority over the ejector function; (ii) the dwell phase by the boiler feed function momentarily taking priority over the recirculating/cooling function (heat exchange solenoid valve 78); (iii) the sterilization phase by the boiler feed momentarily taking priority over the recirculating/cooling function; (iv) the drying phase by the boiler feed momentarily taking priority over the evacuation function; and (v) the filtered air admission phase by the boiler feed function taking priority over the recirculating/cooling function. The synchronization technique described here may be used equally well in a gravity sterilization cycle.

Gravity Return Condensate Recirculating System

In any steam sterilizer, it is important to provide means for maintaining the walls of the sterilizer chamber at an elevated temperature. This may be accomplished by providing a jacket around the chamber walls and flowing steam through the jacket. Wall temperature also may be maintained by surrounding the chamber with tracing coils and flowing steam through those coils; this arrangement is depicted in the drawings.

In either of these chamber wall heating techniques, the condensate formed from the collapse of steam during the heat exchange process ordinarily is passed through a steam trap to an external drain. In a closed loop steam sterilizer of the type described herein, however, any discharge of condensate formed in the tracing coils to an external drain represents a loss of water from the system and, a consequent depletion of boiler feed water.

Figure 6:
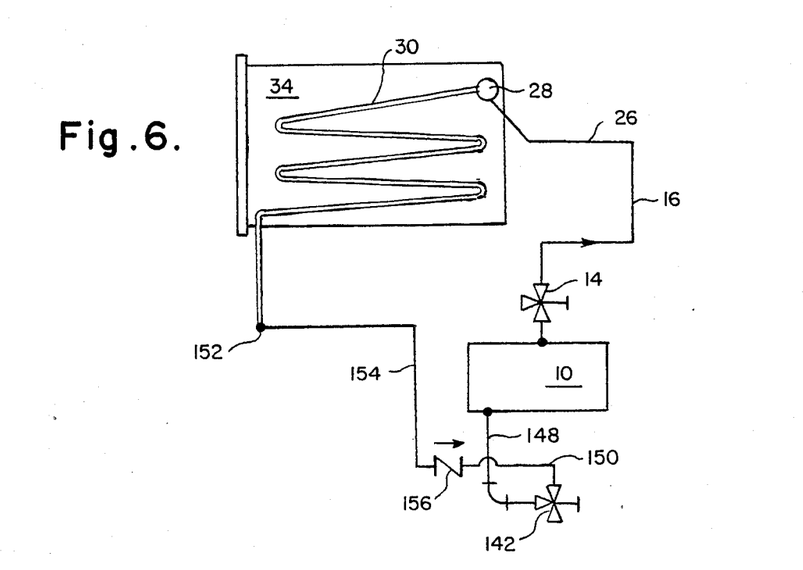
FIG. 6 is a schematic of components shown in FIG. 1 that comprise a gravity return condensate recirculating system for the sterilizer chamber wall heating means.

Referring to FIG. 6, there is shown a gravity return condensate recirculating system which assures that any condensate formed in the tracing coils 30 is returned to boiler 10 as hot water. Steam generated in boiler 10 passes upwardly through valve 14, through lines 16 and 26, and into manifold 28. From there, the steam is distributed to tracing coils 30 which are arranged to slope downwardly from manifold 28. Any condensate formed in tracing coils 305 flows by gravity to collection point 152, through line 154, through check valve 156, into shutoff valve 142 through line 150, and into boiler 10. To the extent that any portion of the path just described is shown in the drawings as being upwardly extending, that is for purposes of the schematic showing only; the path for condensate to flow from manifold 28 through tracing coils 30 to boiler 10 is a "downhill" path.

Similarly any condensate that forms in the steam supply path to manifold 28 flows by gravity through lines 26 and 16, through shutoff valve 14 and into boiler 10.

The use of a gravity return system for hot condensate eliminates the need for an expensive hot condensate pump and reservoir as may have been employed in known self-contained steam sterilization systems.

Method for Combining Fluid Flow From the Sterilizer Chamber Evacuation Circuit With Water Flowing in the Recirculation/Cooling Circuit In a closed loop sterilizer system, the heat from the steam in the chamber must be absorbed each time the chamber is evacuated. Typically, the heat absorption medium is water flowing through an ejector being used to create the low pressure needed for evacuation. As the steam condenses upon contact with the flowing water, the temperature of the water is raised and this heat must be dissipated through a heat exchanger circuit in order to prevent eventual boiling of the water and loss of water in the system through evaporation.

Figure 7:
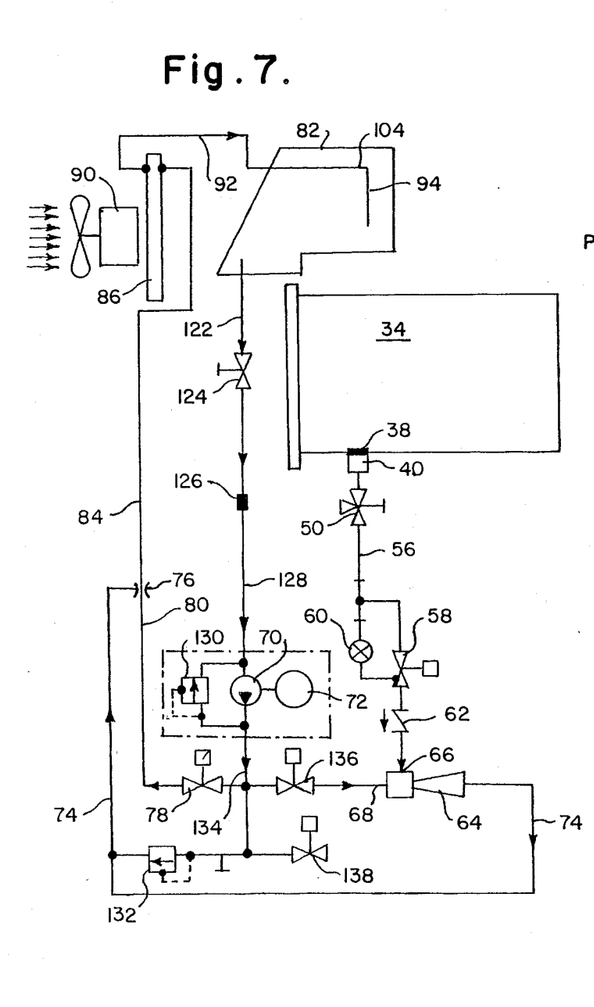
FIG. 7 is a schematic of components shown in FIG. 1 that are used to combine fluid flow from the chamber evacuation circuit with flow in the recirculation/cooling circuit.

Referring to FIG. 7, it may be seen that the closed loop sterilizer depicted there employs a single pump 70 to serve (i) the boiler feed function through boiler feed solenoid valve 138; (ii) the chamber evacuation function through ejector solenoid valve 136; and (iii) the heat exchanger circuit through heat exchange solenoid valve 78. As constrasted with known steam sterilizers which may employ a number of heat exchangers, the present system uses one large capacity heat exchange unit 86. The flow combination feature under discussion, therefore, is to combine the flow of fluids, especially steam, entering the ejector 64 with relatively cool water drawn from water tank 82 and pumped through ejector 64, with the flow of water also drawn from water tank 82 by pump 70 and pumped through heat exchange solenoid 78 on its way to heat exchange unit 86 via lines 80 and 84. An advantage of this arrangement is that the venturi "Y" component 76 creates a suction in line 74 due to the flow of water in 80. This suction enhances the performance of ejection 64 since it virtually eliminates any back pressure that may be transmitted through line 74 to the outlet of ejector 64. In the event ejector valve 136 is closed, venturi "Y" 76 still creates a suction in line 74. If there were no venturi at "Y" 76, a back pressure due to the flow resistance of the heat exchanger could be transmitted through line 74 and ejector 64 to check valve 62. This pressure is relatively small and insufficient to seat check valve 62 so flow would pass through check valve 62. Then, if the sterilizer chamber were not pressurized, this flow would enter the chamber. The temperature of this water will be elevated by the hot chamber and could then result in injury to an operator when door 37 is opened. Also, if a load were left in the chamber, it would become soaked.

There normally is no high pressure in line 84 leading into heat exchange unit 86. The absence of high pressure permits, therefore, the use of high efficiency, relative thin, flat fins in heat exchange core 86.

Water Reservoir for Self-Contained Steam Sterilizer

The self-contained sterilizer described herein is provided with a water reservoir or tank 82 (see FIG. 8) having three sections: a receiving section 98, a settling section 100 and a suction section 102. The design of water tank 82 provides for efficient isolation of particles carried in the water and substantially moisture-free venting of air to the atmosphere.

Figure 8:
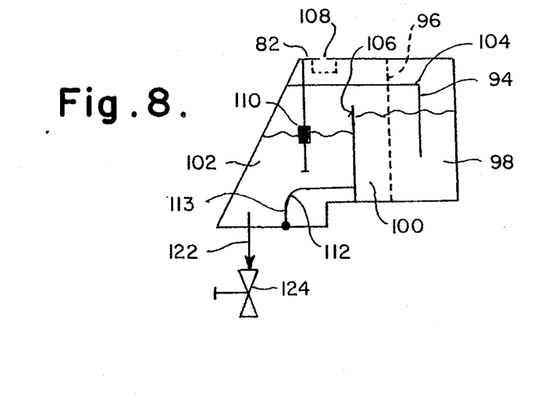
FIG. 8 is a diagrammatic view of the water tank used in the sterilizer shown in FIG. 1.

Water entering water tank 82 flows through line 94 and is discharged beneath the surface of the water in receiving section 98. The presence of air and/or steam in the water so discharged causes considerable turbulence within receiving section 98 but that turbulence is contained by the presence of a screen 96 between receiving section 98 and settling section 100. Thus, the water in settling section 100 is relatively calm. Line 94 also contains a series of vacuum break holes 104 to prevent any siphoning tendency through line 94.

Any air discharged at the surface of the water in receiving section 98 passes to air vent 108, which contains an arrangement of baffles (not shown), and is exhausted to atmosphere. The baffles prevent the exhausted air from carrying with it droplets of water so the water loss through vent 108 is minimized.

Screen 96 prevents the passage of large particulate matter to settling section 100 of water tank 82. The calm water condition present in settling section 100 permits settling of particulate matter that passes screen 96.

Water in settling section 100 flows into suction section 102 by spilling in a thin, broad section over partition (or weir) 106. Such flow promotes the release of any entrained air for venting to atmosphere through vent 108. Water is withdrawn from suction section 102 by pump 70 through line 122 whose inlet end extends above the floor of suction section 102; this arrangement minimizes the possibility of settled particles entering line 122. A two position float switch 110 is mounted in suction section 102 to sense high and low water levels.

A tube 112 is disposed within suction section 102 to facilitate draining of all three sections of water tank 82 through drain valve 114. One end of tube 112 communicates with settling section 100 (and thus with receiving section 98). A series of holes 113 are provided in the vertical segment of tube 112 to allow water flow from suction section 102; the arrangement of holes 113 minimizes the opportunity for settling particles to enter tube 112 during draining.

An important advantage of the particle avoidance measures used in water tank 82 is that they make unnecessary a conventional filter which tends to impede flow and/or create back pressure and thereby adversely affect ejector performance.

Method for Replenishing the Water Tank in a Self-Contained, Closed Loop Sterilizer In a self contained, closed-loop steam sterilizer of the type described herein, it is necessary, from time-to-time to replenish the water in the water tank to bring the system to full capacity. Filling of the water tank can pose a problem to the operator depending upon the particular configuration of the sterilizer. For example, if the sterilizer is supported on a counter, the water tank may be out of convenient reach of the operator and could involve a "blind" filling procedure that could result in spillage on moisture sensitive components of the sterilizer. If the sterilizer is flush mounted in a wall, the water tank may be completely inaccessible from the front of the sterilizer.

Figure 9:
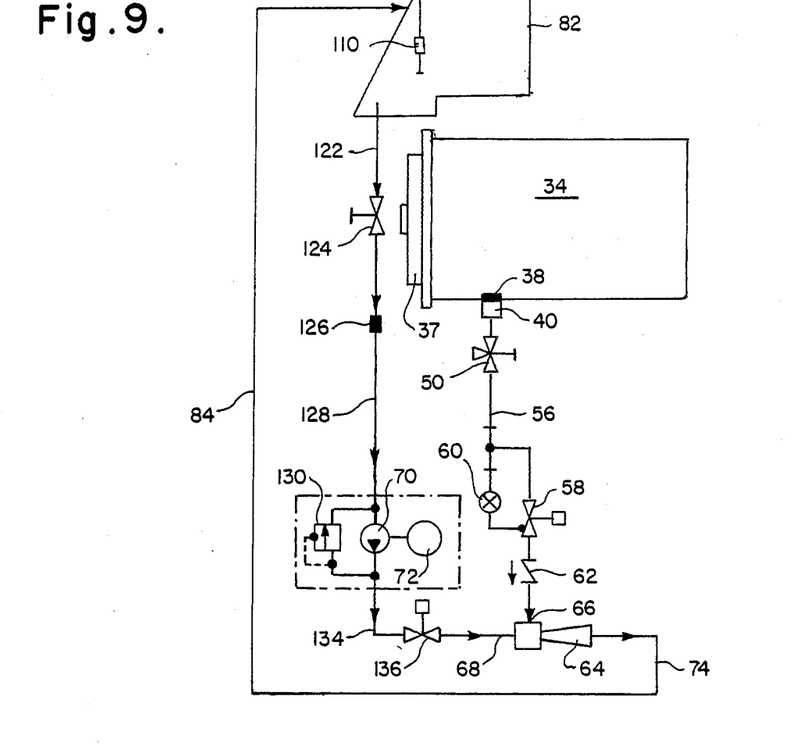
FIG. 9 is a schematic of components shown in FIG. 1 that are used to replenish the water tank in the sterilizer shown in FIG. 1.

Referring to FIG. 9, there is shown a sterilizer chamber 34, forming part of a self-contained, closed-loop system, with water tank 82 located above the chamber. The replenishment of water to water tank 82 is conveniently accomplished by relying on existing components of the system as follows: The operator opens door 37 of chamber 34, the chamber 34 always being accessible to the operator. A water refill control is acutated and water is poured directly into the strainer 38 at the bottom of chamber 34; at the same time, ejector solenoid valve 136 is opened and pump 70 is actuated; water flows from water tank 82 through line 122 and shutoff valve 124, past temperature switch 126, to the inlet of pump 70 through line 138, out of pump 70 through line 134 and ejector solenoid valve 136 via line 134, and into the inlet of ejector 64 through line 68. As water flows through ejector 64, a suction is created at suction port 66 which draws the water poured into strainer 38 past thermister 40, through valve 50 and line 56, through drain solenoid 58, past check valve 62 and into ejector 64; the combined flow passes through lines 74 and 84 to water tank 82. When the float switch 110 indicates that water tank 82 is full, pump 70 is turned off and the operator is signaled to stop pouring water into strainer 38.

After the filling cycle, water tank 82 may be prevented from supporting fungus or algae growth by introducing steam into chamber 34 (after the door 37 is closed), through the recirculating system, and into water tank 82 for the purpose of raising the temperature of the water to at least 150° F. and holding that temperature for a predetermined period.

Method to Improve Sterilizer Steam Quality Using a Qualitizer Orifice

Figure 10:
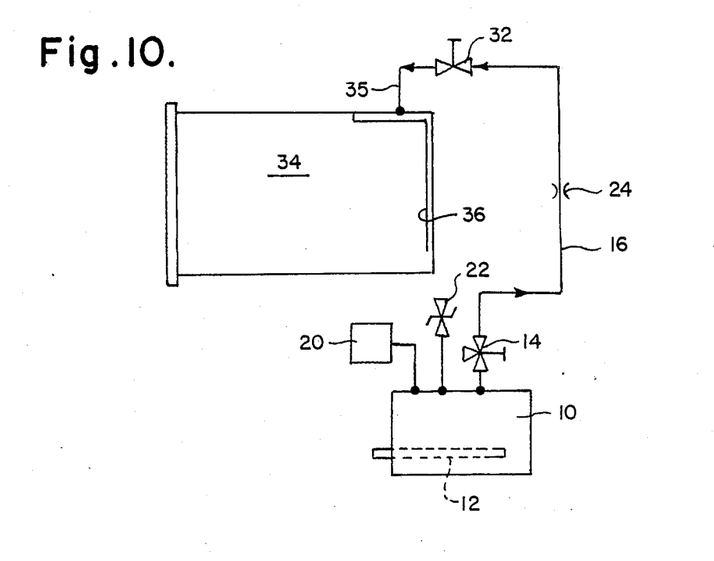
FIG. 10 is a schematic of components shown in FIG. 1 that are used to improve the quality of the steam entering the sterilizer shown in FIG. 1.

Referring to FIG. 10, an orifice 24 is provided in line 16 which conveys steam from boiler 10 to chamber 34 through steam solenoid valve 32. The purpose of orifice 24 is to improve the quality of the steam introduced into chamber 34. According to well-known principles, any water droplets present in the steam passing the orifice will be flashed to steam.

The steam qualitizer orifice 24 is sized so that it will permit a steam flow equal to (or less than) the net steam producing capacity of the steam boiler 10. For example, for a boiler with a net capacity of 6400 Watts (21900 Btu/hour), 18½ lbs. (maximum) of steam per hour can be produced and may pass through this orifice.

Since the boiler capacity is not exceeded, the pressure in the boiler should not fall. However, the pressure in the sterilizer chamber will vary from 0 to 45 psia. An enthalpy balance can be used at this time to convert the minimum recommended steam quality (97%) at the maximum chamber pressure to a minimum boiler/supply steam quality at any given pressure. (Steam quality is the ratio of weight of steam to weight of steam plus entrained water times one hundred percent). A sample calculation follows:

Enthalpy @ 45 psia and 97% quality = Enthalpy @ 114.7 psia and $X$ % quality 243.36 Btu/lb. + .97 (928.6 Btu/lb.) =

308.8 Btu/lb. + $\frac{X}{100}$ (880.0 Btu/lb.)

1144.1 Btu/lb. = 308.8 Btu/lb. + 8.8 $X$ Btu/lb $X$ = 94.97% quality

This same method can be used to produce the following Table I:

TABLE I

| Chamber Pressure | Steam Quality | "Constant" Corresponding Enthalpy | Boiler/Supply Pressure | Corresponding Boiler/Steam Steam Quality |
|---|---|---|---|---|
| 45 psia | 97% | 1144.1 Btu/lb. | 65 psia | 96.2% |
| 35 psia | 97.6% | | 75 psia | 95.8% |
| 25 psia | 98.3% | | 85 psia | 95.5% |
| 14.7 psia | 99.3% | | 95 psia | 95.3% |
| 14.0 psia | 99.4% | | 105 psia | 95% |
| 12.0 psia | 99.7% | | 114.7 psia | 94.9% |
| 10.00 psia | 100.1% | | 125.0 psia | 94.6% |
| 5.0 psia | 101.3% | | 135.0 psia | 94.4% |
| 1.0 psia | 103.7% | | 145.0 psia | 94.3% |
| .2 psia | 105.5% | | | |

Superheated steam is unacceptable for efficient sterilization but it is very useful for bringing a load up to temperature since condensation will occur as heat energy (Enthalpy) is transferred to the load. The boiler steam quality is measured and then a boiler pressure selected that will produce the desired chamber steam quality. If too high a pressure is selected, too much superheated steam can be produced and sterilization can be difficult to achieve.

Depending upon the sterilization temperatures used in a sterilizer, different amounts of superheated steam are tolerable. The following Table II lists sterilization temperature and corresponding pressures:

TABLE II

| Sterilization Temperature | Corresponding Pressure |
|---|---|
| 230° F. | 20.8 psia |
| 250° F. | 29.8 psia |

A sufficient amount of saturated steam should enter the chamber in the conditioning phase prior to reaching sterilization temperature. Thus for a 230° F. sterilization cycle, the steam should cease to be superheated before the chamber reaches 20.8 psia. Once the boiler supply pressure is selected, the orifice size can be determined. Then, steam quality measurements can be made to verify the size.

This system is superior to a conventional steam separator in that it produces high quality steam almost instantly. A separator will produce a wet slug each time it starts up and is not well suited for the short "make-ups" that occur during the sterilizer phase of the sterilization cycle.

This system also restricts the rate of steam flow into the chamber so a steam pressure regulator is not required. The regulator prevents over pressurization in the chamber during the sterilizer control reaction time by restricting flow as its regulating setting is approached.

Furthermore, the quality of steam coming from the boiler is improved by reducing moisture carryover due to large change in boiler outlet pressure. The orifice maintains outlet pressure at a constant level and minimizes moisture carryover.

What is claimed is:

1. A method of steam sterilizing objects in a sealable sterilization chamber, comprising: providing a steam sterilizer cycle having at least one presterilization vacuum pulse, wherein said steam sterilizing cycle comprises
    a first charge phase wherein steam is introduced into a chamber until a predetermined elevated temperature is reached and a drain in said chamber is closed;
    a dwell phase wherein said predetermined elevated temperature is maintained at a substantially constant level;
    a vacuum pulse wherein said drain is opened and steam is not introduced;
    a second charge phase;
    a sterilization phase;
    a vacuum pulse; and
    a drying phase.

2. The cycle recited in claim 1 further comprising, prior to the first charge phase, a start up charge of steam wherein steam is introduced into said chamber while said drain is open followed by an initial vacuum pulse wherein said drain remains open and steam is not introduced into said chamber.

* * * * *

UNITED STATES PATENT AND TRADEMARK OFFICE
CERTIFICATE OF CORRECTION

PATENT NO. : 4,909,988

DATED : March 20, 1990

INVENTOR(S) : Robert W. Childers and James R. Rickloff

It is certified that error appears in the above-identified patent and that said Letters Patent is hereby corrected as shown below:

Col. 2, line 4, delete "." after means and substitute therefor --;--.

Col. 2, line 32, delete "guage" and substitute therefor --gauge--.

Col. 11, in Table I, delete "105.5%" in the first column entitled "Chamber Pressure" and insert --105.5%-- in the second column entitled "Steam Quality" after "103.7%".

Col. 12, line 21, delete "sterilizer" and substitute therefor --sterilizing--.

Signed and Sealed this

Fourth Day of June, 1991

Attest:

HARRY F. MANBECK, JR.

Attesting Officer

Commissioner of Patents and Trademarks